United States Patent [19]
Moriarty et al.

[11] 3,972,860
[45] Aug. 3, 1976

[54] L-ASPARTYL-L-PHENYLGLYCINE ESTERS OF LOWER ALKANOLS

[76] Inventors: Carole L. Moriarty, 359 Huntington Ave., Buffalo, N.Y. 14212; George L. Tritsch, 108 Lexington Ave., Buffalo, N.Y. 14222

[22] Filed: Sept. 2, 1969

[21] Appl. No.: 854,786

[52] U.S. Cl. ............................ 260/112.5 R; 426/548
[51] Int. Cl.² ................. C07C 103/52; A23L 1/22
[58] Field of Search ................................. 260/112.5

[56] References Cited
UNITED STATES PATENTS

| | | | |
|---|---|---|---|
| 3,264,280 | 8/1966 | Hofmann et al. | 260/112.5 |
| 3,299,035 | 1/1967 | Boissonnas et al. | 260/112.5 |
| 3,450,687 | 6/1969 | Hobbs | 260/112.5 |
| 3,475,403 | 10/1969 | Mazur et al. | 260/112.5 |
| 3,492,131 | 1/1970 | Schlatter | 99/141 |

OTHER PUBLICATIONS

Bergmann et al., Chem. Ber. 65, 1198 (1932).
Mazur et al., J. Am. Chem. Soc. 91, 2684–2691 (1969).
Anderson et al., Acta Chim. Akad. Sci. Hung. 44, 187–195 (1965).
Bergmann et al., Chem. Ber. 65, 1196–1197 (1932).
Zaoral et al., Coll. Czech. Chem. Commun. 24, 2010 (1959).

*Primary Examiner*—Lewis Gotts
*Assistant Examiner*—Reginald J. Suyat
*Attorney, Agent, or Firm*—Bean & Bean

[57] ABSTRACT

L-aspartyl-L-phenylglycine esters, e.g., L-aspartyl-L-phenylglycine methyl ester, are new compounds useful as sweeteners for various foods, beverages and compositions intended to be tasted, e.g., chewing gums, dentifrices, mouth washes. Such compounds can be made by reaction of a corresponding amide, such as asparagine, with an amino blocking agent, e.g., carbobenzoxy chloride, whereby a reaction with the amino group of the asparagine produces the corresponding carbobenzoxyamide, following which the amide is reacted with the methyl or other suitable lower alkyl ester of an amino acid, e.g., phenylglycine, to produce the corresponding peptide by reaction of the free carboxylic and amino groups, and subsequently, the carbobenzoxy group is removed by hydrogenolysis in the presence of a catalyst and the terminal amide of the peptide is converted to the corresponding acid by hydrolysis.

2 Claims, No Drawings

L-ASPARTYL-L-PHENYLGLYCINE ESTERS OF LOWER ALKANOLS

DESCRIPTION OF THE INVENTION

Artificial sweeteners presently constitute an important proportion of all sweetening materials sold. The millions of pounds of such sweeteners produced annually are the equivalent of nearly a billion pounds of sucrose. The rate of production of artificial sweeteners is increasing, primarily because their low caloric values make them useful in low-caloric or diet foods and drinks and in sugarless but desirably sweet products, such as chewing gums and oral preparations.

Like many other biological properties of chemical compounds, taste has been found to be generally unpredictable from chemical structure. Thus, very small changes in chemical compositions may significantly affect the tastes thereof. Comparatively few synthetic chemical compounds are known which exhibit sweetness and which can be employed in place of the sugars, with comparable tastes and the required absence of objectionable aftertaste, bitterness and other undesirable properties. Those compounds which have been successfully employed, such as the cyclamates and saccharins, are structurally different from the peptides of the present invention. In fact, few peptides are known which possess sweetening properties and of these, fewer yet are very much more sweet than sucrose. Some such peptides are described in an article by Mazur et al., appearing at volume 91, pages 2684–2691 of the Journal of the American Chemical Society (1969). This article mentions the making of esters of aspartylphenylalanine, compounds which may be considered to be structurally analogous to the present glycine esters. The syntheses of such phenylalanine derivatives are described in the Journal of the Chemical Society (C), London, 1966 in an article by Davey, et al., at pages 555–566.

Although in the above articles, other structurally related sweetening materials are described, together with methods for their manufacture, the present compounds and the present simplified method for their manufacture are not mentioned or suggested. In addition to being satisfactory artificial sweeteners, the present products are considered to be possessed of significant advantages over the closest prior art compounds known to the inventors because the phenylglycine portion of the invented compounds is not metabolized or incorporated into protein, as is phenylalanine. Thus, the phenylglycine peptides of this invention may be employed in instances where the phenylalanine compounds would be objectionable, such as in sweetening foods and beverages for children afflicted with phenylketonuria or patients with other diseases or bodily conditions adversely affected by phenylalanine reactions with body proteins. Furthermore, the fact that the phenylglycine portions of the present compounds are not metabolized and are excreted indicates their non-interference in the present compounds with body processes, as compared to other sweeteners.

In accordance with the present invention, new compounds possessing sweetening properties have been discovered which are the lower alkyl esters of L-aspartyl-L-phenylglycine. Of these, the methyl ester is most preferred. Such compounds are useful for sweetening foods and beverages, and also other materials intended to be taken into the mouth and in which taste is important, e.g., chewing gum, dentifrices, mouth washes. Also within the invention are methods for the manufacture of such compounds and related materials of peptide structure, wherein an amino blocking group, such as a carbobenzoxy group is employed to protect the free amine of an amino acid having another carboxylic acid amide group, after which the compound resulting is reacted with the amino group of an amino acid ester and the product resulting has the carbobenzoxy group removed and the other amide group converted to the corresponding acid. In a preferred embodiment of this invention, the amino acid in which the amino group is protected, is L-asparagine, and the other amino ester is an L-phenylglycine ester.

The lower alkyl esters of L-aspartyl-L-phenylglycine include those of 1 to 3 carbon atoms and greatest sweetening effect is noted with the methyl ester. It is within the inventive concept to employ compounds of equivalent structures containing non-interfering substituents but normally only the unsubstituted alkyl esters will be used and most of the time, for greatest sweetening effect, the methyl ester will be employed. Although the various other parts of the molecule are considered to be most important with respect to sweetening action, it has been noted that different esterifying groups may be employed, including alkenols, such as vinyl and allyl alcohols, as esterifying reactants, to obtain products of the aspartylphenylglycine ester type. Such compounds are convertible to the corresponding alkyl esters by hydrogenation or known reactions.

The artificial sweeteners of this invention are generally of relatively low acidity, with a 1% solution thereof usually exhibiting a pH in the range of 3 to 7. Accordingly, they are suitable for sweetening various acidic beverages, such as soft drinks, ades, tea and coffee, as well as more neutral beverages, including milk and non-carbonated flavored water. Although highly basic or acidic aqueous media tend to promote hydrolysis of ester bonds, the present compounds are of sufficient stability to make them acceptable as sweeteners for the usual beverages. Similarly, they may be employed to sweeten foods, such as puddings, gelatin, ice cream, cookies, cakes, pies, vegetables, rolls, breads, sauces, meats, e.g., ham, fruits, berries, syrups, cereals, etc. Because the sweetening effect of the present materials may be from 10 to 1,000 times the sweetness of ordinary cane or beet sugar, or sucrose, very small amounts of the sweetener will need to be employed. Usually, such quantity will be from 0.0001% to 1% of the weight of the food or beverage. Generally, the proportions of sweetener will be from 0.001 to 0.1% of the unsweetened material, although other ranges of proportions may also be used, depending upon the degree of sweetness desired, the type of material being sweetened, the presence or absence of other sweetening agents and the activity of the particular artificial sweetener of this invention being employed. The present sweetener may be used in mixture with other accepted sweetening agents, whether caloric or of the low-calorie type. Thus, it may be mixed with sucrose, cyclamates, e.g., calcium cyclamate, or saccharins. Similar ranges of proportions of the present compounds may be employed in oral preparations other than food and beverages, such as chewing gums, dentifrices and mouth washes.

Addition of these sweeteners may be made by any of the normal means employed for adding other similar materials. Thus, they may be added at the time of use or at the times of preparation or cooking of the various products and may be applied as dilute solutions or as powders. Because phenylglycine is not absorbed by the body, these materials may be used for their sweetening activity in many applications wherein other compounds would be suspect, because of their absorption by the body or incorporation into body proteins. Low toxicity, due in part to such non-absorption, is an important advantage of the present compounds.

The artificial sweeteners are capable of being manufactured by comparatively inexpensive and readily practiced methods. Thus, by appropriate selection of a starting reagent and by following the manufacturing method of this invention, L-aspartyl-L-amino acid esters may be produced by a method which includes carbobenzoxylation of the amine group of asparagine, to protect that group, after which an ester of the amino acid reactant is reacted with the asparagine compound to produce the corresponding dipeptide by reaction of the free carboxylic acid and amino groups. This is followed by the removal of the carbobenzoxy group according to known methods and by conversion of the amide of the asparagine to an acid group. Although primarily intended for use with L-phenylglycine or L-phenylalanine, the present method is also applicable to the production of other peptides of aspartic acid with any other suitably protected amino acid. By suitably protected is meant that the carboxyl group(s) is esterified and only one amino group to be reacted is free. Such amino acids include alanine, valine, tyrosine, leucine, methionine, arginine, lysine. They may be substituted by alkyl, aryl (phenyl), benzyl and other suitable substituents.

Instead of benzyloxy carbonylation, to add the radical $C_6H_5CH_2OCO-$ to the amino group of asparagine, other protective radicals for the amine may also be added, such as p-nitrocarbobenzoxy, tertiary butyloxy carbonyl, acetyl, phthalyl, benzoyl, trityl, etc. Other equivalent or similar methods, using other known blocking groups for the amine may be used. To obtain the sweetening compounds of this invention asparagine should be employed but the method of manufacturing the dipeptides is also applicable to the various other monocarboxylic acid amides of amino dicarboxylic acids, such as isoasparagine, glutamine, isoglutamine, etc. Thus, while the process is particularly applicable to the manufacture of L-aspartyl-L-phenylglycine methyl ester and L-aspartyl-L-phenylalanine methyl ester, the principles thereof are applicable to the manufacture of dipeptides of monoamides of monoaminodicarboxylic acids and monoaminomonocarboxylic acid esters. In such reaction, the amino group of the monoamide of the monoaminodicarboxylic acid is blocked, the resulting compound is reacted with the monoaminocarboxylic acid ester, the blocking group is removed and the amide radical (not the peptide amide) is converted to a carboxylic acid. Such a method is superior to one in which a dicarboxylic monoamino acid is employed as a starting reagent. In such a more usual case, it is necessary to block both carboxyl groups as well as the amine. Often this requires a careful and selective removal of one of the carboxyl-blocking groups so as to allow formation of the peptide by reaction of the resulting unblocked single carboxylic acid group with the amine of an amino acid. For example, such a reaction might involve reacting benzyl alcohol with aspartic acid to form the dibenzyl ester. Then, this is reacted with carbobenzoxy chloride, to protect the amine group of the aspartic acid diester. Subsequently, the desired carboxylic acid group must be made available by selective removal of one esterifying benzyl group, after which the remaining compound is reacted with the amino acid, e.g., phenylglycine, to form a dipeptide, and the other benzyl group is removed, leaving the free acid. As will be noted, such a synthesis is longer and more difficult than the new method of this invention.

The equations for the present reactions, in a general form may be shown as:

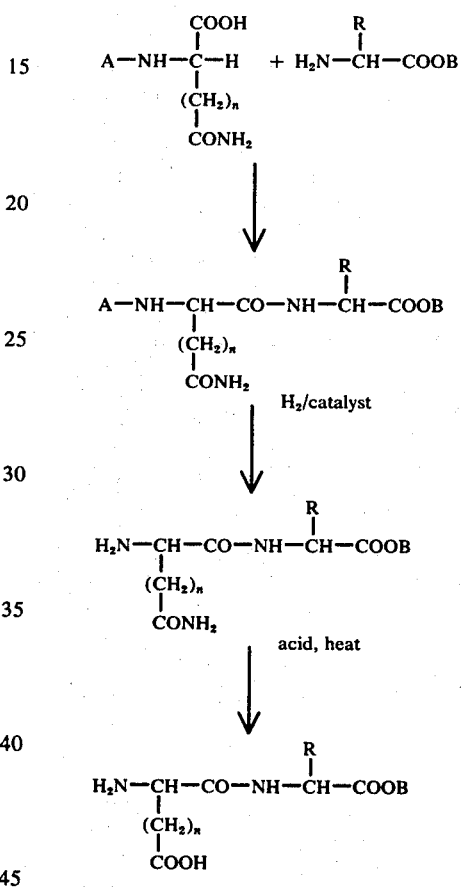

In the above, A represents carbobenzoxy or an equivalent blocking group, B is an esterified group, R is alkyl or aryl (preferably phenyl), and n is a number from 0 to 10.

For the various reactions shown, the proportions of reagents employed will be in accordnce with the usual practice. Generally, from a 20% deficiency to a 20% excess of stoichiometric quantities of reagents will be used, although in some instances a greater excess might be desirable. The usual catalysts for the various reactions and the ordinary mechanisms for effecting them may be employed. Thus, for example, the coupling of the two amino acid compounds will normally be by the diimide mechanism, using dicyclohexylcarbodiimide. However, other coupling mechanisms such as those using one of the many available mixed anhydrides, may be substituted. The product may be purified, as by recrystallization from a solvent. The carbobenzoxy group may be removed by catalytic hydrogenation, using a palladium catalyst, such as palladium black on charcoal. The amide group is removable by hydrolysis, preferably with heating, with acid, e.g., 0.1 N HCl. Of course, the final product may be purified by various methods, including freeze drying and recrystallization from suitable solvents.

The following examples are furnished to illustrate preferred embodiments of the invention. They are not to be considered to limit the invention. All parts given are by weight, unless otherwise indicated.

EXAMPLE 1

1.31 parts L-asparagine are stirred with 100 parts water, and 1.7 parts carbobenzoxy chloride and 2.5 parts of 4N NaOH are added. After 1 hour of stirring, the mixture is extracted with ether, the aqueous layer is acidified and the product is filtered off. It is recrystallized from hot water and the purified product, carbobenzoxy L-asparagine, melts at 163°–165°C. (uncorrected).

2.65 parts of L-phenylglycine, obtained by resolution of the D,L-acid with hog kidney acylase, are suspended in 100 parts methanol, cooled to −10°C., and an excess, 1.6 parts of thionyl chloride, is added drop-wise. The mixture is allowed to warm to room temperature and is boiled at reflux for 2 hours. The solvent is evaporated in vacuuo and the product, L-phenylglycine methyl ester hydrochloride, is crystallized from ethanol. It has a melting point of 156°–157°C.

2 parts of the L-phenylglycine methyl ester hydrochloride are added to 50 parts of dimethylformamide. 1.4 parts of triethylamine are added and after cooling to 0°C., 2.66 parts of carbobenzoxy L-asparagine, dissolved in 50 parts dimethylformamide, are admixed with the ester solution. While maintaining cooling with an ice bath, 2.06 parts of dicyclohexylcarbodiimide, dissolved in 10 parts of dimethylformamide, are then reacted with the mixture. After 10 minutes, the ice bath is removed and the solution is allowed to reach room temperature, and is maintained there overnight. The formed byproduct, dicyclohexyl urea, is removed by filtration and the remaining solvent is evaporated in vacuuo. The product is filtered off and washed with cold water, followed by a cold 5% NaHCO₃ aqueous solution, cold 10% HCl aqueous solution and cold water.

The washed product carbobenzoxy L-asparaginyl-L-phenylglycine methyl ester, is then dried and recrystallized from hot ethyl acetate. It is a white powder with a melting point of 191°–194°C., obtained in almost stoichiometric amount.

The carbobenzoxy group is removed by hydrogenating 1 part of the above dipeptide in 50 parts methanol with 0.1 part of palladium black on charcoal catalyst at atmospheric pressure and room temperature for 2 hours. After filtration and evaporation, the product is suspended in 50 parts of 0.2 N HCl and heated at 100°C. for 2 hours. The resulting L-aspartyl-L-phenylglycine methyl ester is obtained in almost stoichiometric amount. Its melting point is 88°C. (decomposes). The composition is verified by amino acid analysis. It is a free-flowing white powder, about 100–1,000 times as sweet as sucrose, with a slight citrus flavor. It is not bitter and gives no aftertaste.

When stoichiometric equivalents of the lower aliphatic esters are substituted for the L-phenylglycine methyl ester, also as the hydrochlorides or other suitable hydrohalides, after neutralization the reaction results in the production of the corresponding lower aliphatic esters of L-aspartyl-L-phenylglycine, e.g., the ethyl and isopropyl esters.

The ethyl and isopropyl esters may be employed as flavoring agents for foods, beverages and oral preparations but the methyl ester is much sweeter, being estimated to be from 100 to 1,000 times as sweet as sucrose. The sweetness of the methyl ester is a pleasant one, having a very slight citric flavor, making it ideal for use as a sweetener for soft drinks. The other esters may also be employed in the syntheses of other peptides, hormones and derivatives, useful in protein research. They may also be converted to the methyl ester.

When asparagine is replaced by glutamine, isoglutamine or isoasparagine, the corresponding dipeptides result by following the process of the above example, with the use of a stoichiometric equivalent of the replacement. Similarly, when an equivalent proportion of other amino blocking radical, such as tertiary butyloxy carbonyl or trityl is used, and later removed by either trifluoroacetic acid or dilute acid respectively, the reaction results in production of the desired peptide. The process of the example is also operative when the L-phenylglycine is directly employed instead of starting with the hydrochloride. Similarly, when hydrogenolysis or hydrolysis reactions are effected for other times, e.g., from ½ to 5 hours, as when the amide group of the L-asparaginyl-L-phenylglycine methyl ester, is removed by boiling at reflux for from ½ to 2 hours in the presence of dilute strong acid, when other catalysts are used to promote hydrogenolysis, and when the carbobenzoxylation is effected by the alternate addition of carbobenzoxy chloride and alkali to the asparagine over various time periods, e.g., 1 to 2 hours, the desired product is also produced. This is also the case when the coupling of the acid and amine groups to form the dipeptide is by another mechanism, such as the mixed anhydride mechanism.

EXAMPLE 2

A carbonated beverage which is cola flavored is sweetened with L-aspartyl-L-phenylglycine made according to the method of Example 1. No other sweetener is employed but due to the great sweetening power of the new compound, only 0.02 to 0.2 grams are required, per 8 oz. bottle. The same percentages satisfactorily sweeten coffee, other soft drinks, chocolate milk, cookies, cereals, fruits and sauces. Lesser proportions, such as 0.005 to 0.015 grams per 8 Oz. are used for flavoring rolls, vegetables and meats, while more, e.g., from 0.025 to 0.8 g./8 oz. may be used for syrups, candies and ice cream. Oral preparations, such as toothpastes, mouthwashes and chewing gums may be sweetened with from 0.01 to 0.1 g./8 oz.

The sweetened products have a pleasant sweetness, like that flavor imparted by sucrose. Sometimes, a faint but pleasant lemon or citrus flavor may be detected.

The invention has been described with respect to various embodiments and illustrations but it is clear that it is inclusive of all other embodiments, which are within the spirit of the present disclosure and which include equivalents of the various elements of the present processes or compositions.

What is claimed is:

1. A dipeptide of the formula:

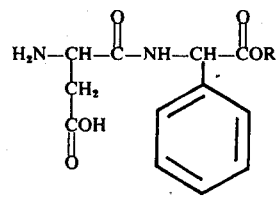

wherein each amino acid is in the L-configuration and R is lower alkyl.

2. L-aspartyl-L-phenylglycine-O-methyl.

* * * * *